United States Patent [19]

Ash et al.

[11] Patent Number: 4,995,268

[45] Date of Patent: Feb. 26, 1991

[54] METHOD AND APPARATUS FOR DETERMINING A RATE OF FLOW OF BLOOD FOR AN EXTRACORPOREAL BLOOD THERAPY INSTRUMENT

[75] Inventors: Stephen R. Ash, Lafayette; Terrance G. Echard, West Lafayette, both of Ind.

[73] Assignee: Ash Medical System, Incorporated, West Lafayette, Ind.

[21] Appl. No.: 402,073

[22] Filed: Sep. 1, 1989

[51] Int. Cl.⁵ ............................................. G01F 1/704
[52] U.S. Cl. .................................. 73/861.05; 210/87; 210/647; 604/4; 604/65; 604/67
[58] Field of Search ........................... 73/198, 861.05; 210/647, 87, 743; 604/4, 65, 67

[56] References Cited

U.S. PATENT DOCUMENTS

| | | | |
|---|---|---|---|
| 3,403,555 | 10/1968 | Versaci et al. | 73/861.05 |
| 3,970,097 | 7/1976 | Voellmy et al. | 73/861.05 |
| 4,135,819 | 1/1979 | Schmid-Schonbein | 356/39 |
| 4,186,601 | 2/1980 | Maruoka | 73/861.05 |
| 4,201,470 | 5/1980 | Ehrly et al. | 356/39 |
| 4,231,871 | 11/1980 | Lipps et al. | 210/87 |
| 4,312,341 | 1/1982 | Zissimopoulas | 604/67 |
| 4,316,391 | 2/1987 | Tickner | 73/861.25 |
| 4,458,539 | 7/1987 | Bilstad et al. | 73/861 |
| 4,661,246 | 4/1987 | Ash | 210/87 |
| 4,764,166 | 8/1988 | Spani | 604/65 |

FOREIGN PATENT DOCUMENTS 2083612 3/1982 United Kingdom ............. 73/861.05

OTHER PUBLICATIONS

Ash et al., "Clinical Trials of Biologic-HD: Automated Single Access, Sorbent-Based Dialysis," Trans ASAIO, vol. 33, 1987, pp. 524–531.

Ash et al., "The Biologic-HD: Hemodialysis Simplified," *Artificial Organs: Proceedings of the International Symposium on Artificial Organs, Biomedical Engineering, and Transplantation in Homor of the 75th Birthday of Willem J. Kolff,* VCH Publishers, N.Y., 1987, pp. 263–277.

Tomita et al., "RBC Aggregometer Head as a Warning Monitor of Flow Disturbance in Extracorporeal Systems," *The International Journal of Artificial Organs,* vol. 10, No. 5, 1987, pp. 295–300.

Primary Examiner—Herbert Goldstein

[57] ABSTRACT

Method and apparatus for determining the flow rate of blood passing between a patient and an extracorporeal therapy instrument. The flow measurement apparatus includes a delivery unit for producing a saline bolus interface at a first position of a measurement channel having a predetermined volume between the first and second position. A sensor unit included in the apparatus detects the saline bolus interface as it passes the second position in the channel. An output signal from the sensor unit along with an indication of the production of the saline bolus interface is utilized by a control unit to determine the blood flow rate. The control unit of the apparatus utilizes instantaneous and average blood flow algorithms to calculate instantaneous and average blood flow rates based on the time interval associated with the production of the saline bolus interface and its progression to a predetermined position in the measurement channel. Successive interfaces are also produced in the blood flow to derive an average blood flow rate.

30 Claims, 4 Drawing Sheets

METHOD AND APPARATUS FOR DETERMINING A RATE OF FLOW OF BLOOD FOR AN EXTRACORPOREAL BLOOD THERAPY INSTRUMENT

TECHNICAL FIELD

This invention relates to medical devices such as extracorporeal blood therapy instruments and particularly to method and apparatus for determining the rate of blood flow for such instruments.

BACKGROUND OF THE INVENTION

When organs of the body fail, various toxins accumulate in the body while other chemicals become deficient. When organ failure is severe, the patient becomes ill. To support the patient, one option is to remove blood and pass it through an extracorporeal blood therapy (EBT) instrument. The instrument typically includes a membrane unit for diffusing or convecting toxins out of the blood into a dialysate fluid or into solid absorbants which selectively absorb the toxins. These extracorporeal blood therapy instruments include hemodialysis and hemofiltration machines to treat kidney failure, heart-lung machines, hemoprofusion columns, plasmapheresis machines, and cell separators. Most extracorporeal blood therapy instruments use some type of pump such as a roller pump for removing blood from a vessel through a needle or catheter, propelling it through the membrane unit, and returning it to the body. Creating adequate blood flow through the instrument would seem simple but, in fact, it is complicated by a number of problems. First, the blood flow rate is variable depending upon the blood flow within the cannulated vessel, the internal diameter of the needle or catheter, the viscosity of the blood, the internal diameter of the vinyl tubing typically used with a roller pump, and the revolution rate of the pump. Furthermore, roller pumps are not volumetric. When resistance increases on the input or output line, blood flow rate drops even though the revolution rate of the pump remains constant.

A second problem occurs when the tip of the intravenous needle or catheter pulls the vein wall against the opening therein, suddenly stopping blood flow.

A third problem is when negative pressure created by the blood pump causes air to leak into the instrument, thereby causing foam or bubbles within the blood. The return of air bubbles to the patient could be life-threatening.

Artificial materials making contact with the blood tend to create blood clotting, thus increasing flow resistance through the instrument.

Another problem occurs in manually "priming" the instrument. This necessarily includes inversion of the membrane unit to purge air from the blood and dialysate sides of the membrane unit. This requires careful observation on the part of the operator to assure that all air bubbles have been removed before use of the instrument.

To assure that blood flows through a blood therapy instrument at a prescribed rate, pressure gauges have been previously attached to the upper portion of drip chambers. These drip chambers allow air to separate from the blood and stay in the upper portion of the chamber while blood exits from the bottom portion of the chamber. A change in pressure measured by these gauges indicates a change in flow through the instrument. Alarms for adverse blood flow conditions occur only when the operator has manually set pressure limits close to initial venous and arterial pressure levels when blood is flowing properly. In the absence of these alarms, the operator must manually observe the flow of blood in the tubing to and from the roller pump.

Dialysis operators spend considerable time observing the flow of blood through the tubing and roller pump during routine hemodialysis of patients. This operator observation during initial priming of the instrument with saline is required, because current dialysis monitor devices cannot accurately perform precise blood flow rate measurements and rapid detection of inflow obstructions. Furthermore, these devices cannot determine the number of microbubbles in the inflow blood lines before an air bubble with significant risk is produced, detect air bubbles during priming to indicate when air is completely replaced by priming fluid, and determine the quantity of platelet/fibrin aggregates leaving the blood therapy instrument to detect dialyzer clotting at a time when increasing anticoagulant would prevent further clotting.

In addition to the above problems, there are a number of problems associated with fluid replacement during extracorporeal blood therapy. The unidirectional movement of blood through a therapy instrument is simply and directly performed by a roller pump, in which rollers move circularly and compress a resilient cylindrical tube. This motion draws blood through one needle or catheter lumen from a patient, propels it through the tubing and membrane package, and returns it to the patient through another needle or catheter lumen. In reality, though, the tubing set is more complicated than this. Blood is not the only fluid which must be delivered to the patient. If the patient's blood pressure falls, several hundred cubic centimeters (cc) of saline or colloid solution must be administered. At the end of the dialysis, a similar amount of saline is infused to rinse blood from the dialyzer. During dialysis, the need for an anticoagulant is diminished by rinsing blood from the dialyzer with 100 ml of saline each one half hour, the "low heparin rinse" schedule. Finally, many blood products and medications are most easily and effectively delivered intravenously during dialysis.

In present dual-needle blood therapy procedures such as hemodialysis, there are a number of manual methods for effectively delivering sterile fluid into blood within the therapy instrument. However, these methods have several significant problems. The negative pressure in the arterial line is variable, thus producing a variable fluid flow rate. The amount of delivered fluid depends upon the flow rate and time of infusion, both of which are not exactly known. Furthermore, there is no device to measure the exact amount of fluid delivered to the patient. Simply observing the change in the air-fluid interface within the fluid bag is an inaccurate method for determining the volume delivered. Without close observation, excess fluid can be drawn into the blood circuit, resulting in fluid overload of the patient. Further, if the fluid container empties, air passes into the arterial line and into the dialyzer. If a large volume of air enters the membrane unit, it cannot be quickly or easily removed, and the dialysis procedure must be aborted.

SUMMARY OF THE INVENTION

The foregoing and other problems are solved, and a technical advance is achieved by illustrative method and apparatus for determining the rate of flow of blood in a flow measurement channel typically leading to an extracorporeal blood therapy instrument. This method and apparatus advantageously ensures that blood returning to a patient is safe and that the blood flow is sufficient. The illustrative apparatus includes a delivery unit for producing an interface between the incoming blood and another fluid, such as saline, at a first position in the channel. The apparatus also includes a sensor unit for producing an output signal indicative of when the interface has reached a second position in the channel. The measurement channel has a predetermined volume between the first and second positions. Also included is a control unit utilizing an indication of the channel volume and a predetermined algorithm for calculating the blood flow rate through the channel in response to an indication of the production of the interface and the sensor output signal.

The delivery unit includes a clamp, such as a processor-controlled roller clamp unit, for selectively administering a bolus of saline to the blood for producing the interface. More particularly, the delivery unit includes first and second flexible vinyl tubes for transporting blood and fluid therein. One tube transports patient blood. The other tube transports the saline fluid from a source thereof. A T-connector positioned in the blood line is utilized for inserting a bolus of saline fluid into the blood for producing the interface. The clamp unit includes a clamping cavity and a roller that is eccentrically mounted to a motor and positioned between the two vinyl tubes in the clamping cavity. The roller selectively compresses the two tubes and occludes the flow therein for inserting a bolus of the saline fluid into the blood and producing the interface. The delivery unit also includes an electric motor controlled by the control unit for operating the roller.

The sensor unit includes a photoemitter for directing an optical signal having a predetermined intensity into the channel at the second channel position. A photodetector, responsive to the intensity of the optical signal transmitted through the channel, produces an output signal indicative of when the interface is at the second position. A change in the intensity of the optical signal due to the blood/saline interface passing through the optical signal in the channel is indicative of when the interface is at the second position in the channel. This photodetector is also responsive to the optical signal transmitted through the channel for producing a second output signal indicative of bubbles in the blood or saline fluid.

The sensor unit also includes a second photodetector responsive to the optical signal reflected from the channel for producing third and fourth output signals indicative of particles in the blood and the pulsating flow of the blood, respectively.

The control unit of the apparatus includes a timer for determining a time period initiated by an indication of the production of the interface by the delivery unit and terminated by the sensor output signal indicating when the interface is at the second position in the channel. The control unit also includes a processor that utilizes a predetermined algorithm for calculating the blood flow rate as a function of the sensed time period and the volume of the channel. The control unit is further responsive to the second through fourth output signals for determining a quantity for the bubbles, particles, and pulsating blood flow, respectively.

A display unit coupled to the controller is also included in the apparatus for displaying the calculated blood flow rate.

To advantageously provide both instantaneous and average accurate blood flow rates, the control unit includes a temporary memory for storing a plurality of successive time periods each of which is initiated by an indication of the production of the successive interfaces in the blood. The processor also utilizes a second algorithm for calculating an average blood flow rate in response to the time periods associated with successive interfaces.

To control the volume of fluid infusion and provide alarms if conditions of the fluid flow become dangerous, a second sensor unit and weight measuring device are included with the apparatus for detecting the delivery and determining the amount of the saline fluid delivered to the channel, respectively. The second sensor unit includes a photoemitter and photodetector positioned on opposite sides of a saline fluid delivery tube for detecting the presence of saline in the tube. Advantageously when an air-saline interface passes the sensor, a large AC signal is generated followed by a DC signal different from that produced by saline when air displaces the saline in the tube.

The weight measuring device comprises a strain gauge comprising a plurality of surface-mounted resistors whose electrical resistance changes in proportion to deformation. The strain gauge accurately measures changes in weight of, for example, the saline fluid bag, thereby accurately reflecting the volume of fluid removed therefrom.

A third sensor, similar to the first sensor, is also advantageously positioned across the venous line to detect blood flow, particles, bubbles, etc. and produce signals indicative thereof. This sensor is utilized to detect problems produced by the blood therapy instrument and to reduce risk conditions to the patient.

The method for determining the rate of flow of blood in the channel includes producing an interface between the blood and another fluid, such as saline, at a first position in the channel and a first indication of the production thereof and producing a second indication of when the interface is at a second position in the channel. The channel has a predetermined volume between the first and second positions. The method further includes calculating the rate of flow of the blood in the channel utilizing a predetermined algorithm, an indication of the channel volume, and the first and second indications of the interface.

The calculation of the blood flow rate includes determining a time period between the first and second indications of the interface and calculating the blood flow rate utilizing the channel volume and the determined time period.

To calculate an average blood flow rate, the method further comprises producing a plurality of the interfaces and indications thereof: producing an indication of when each of the interfaces is at the second position in the channel; determining a plurality of time periods, each associated with the production of an interface and an indication of when it is at the second position in the channel; and calculating an average rate of flow of the blood utilizing a second algorithm incorporating the channel volume and the plurality of time periods.

The production of an interface includes selectively administering a bolus of the saline fluid to the blood. More particularly, the production of the interface includes transporting the blood in the first tube and the saline fluid in the second tube. Also included are interconnecting the first and second tubes with the channel and selectively occluding the blood flow and saline fluid flow in the two tubes.

The production of the second indication of when the interface is at the second position in the channel includes directing an optical signal having a predetermined intensity into the channel at the second position and sensing a predetermined change in the intensity of the optical signal from the channel.

The method further includes visibly displaying the various blood flow rates when calculated.

DETAILED DESCRIPTION

Figure 1:
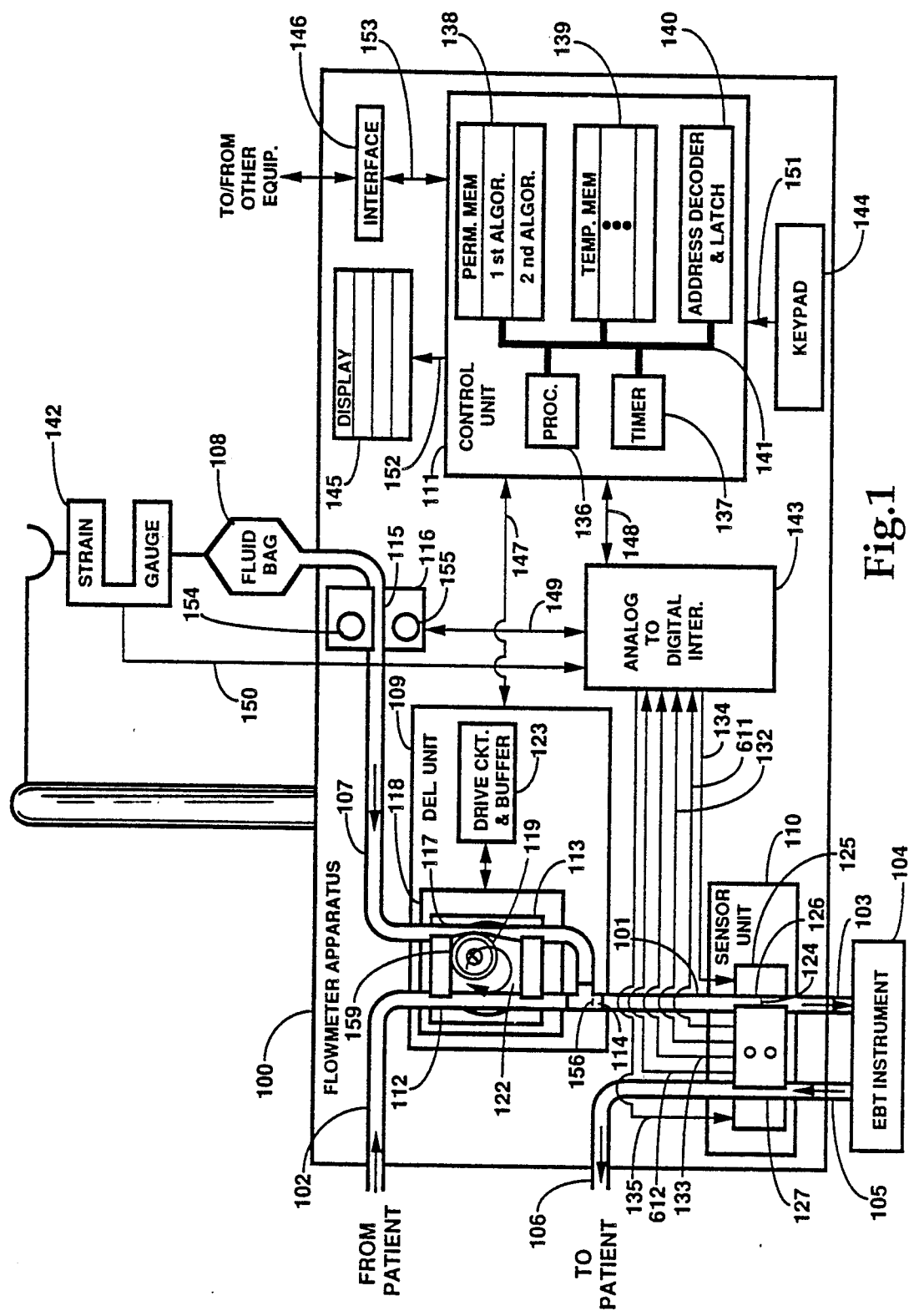
FIG. 1 depicts illustrative flowmeter apparatus of the present invention for use with an extracorporeal blood therapy instrument.

Depicted in FIG. 1 is apparatus 100, also referred to as an optical scattering flowmeter, for determining a rate of flow of blood through a flow measurement channel 101 contained therein. The flowmeter is intended for use with an extracorporeal blood therapy instrument 104 such as a hemodialysis machine for treating patients with kidney failure. Arterial line 102 is connected to a patient for receiving blood from an arterial blood vessel of the patient. Arterial blood from the patient passes through the flowmeter and, in particular, flow measurement channel 101 to arterial input line 103 of the extracorporeal blood therapy instrument 104. Blood therapy instrument 104 includes a membrane unit (not shown) that diffuses or convects toxins out of the incoming blood into a dialysate fluid or solid sorbents, which selectively absorb the toxins. Such an extracorporeal blood therapy instrument is described in detail in U.S. Pat. No. 4,661,246 of one of the present inventors and is commercially available from Ash Medical Systems, Inc., West Lafayette, Ind.

Flowmeter apparatus 100 receives the treated blood via venous output line 105 of the blood therapy instrument. The flowmeter includes a dual-line sensor unit 110 that monitors the treated blood, which returns to a venous blood vessel of the patient via venous line 106.

The flowmeter apparatus monitors the blood passing between the patient and the blood therapy instrument to determine whether the returning blood is safe, and the blood flow therebetween is sufficient. The flowmeter effectively measures several parameters including the minute-to-minute average blood flow rate and the second-to-second changes in blood flow rate, which typically indicates the collapse of the patient's arterial blood vessel around the output needle or cannula. The flowmeter also measures changes in the reflectivity and fluidity of the blood and the number of platelet/fibrin particles leaving the membrane unit of the therapy instrument, which are early indicators that the blood therapy instrument is clotting. Furthermore, the flowmeter also measures foam or bubbles flowing into or out of the blood therapy instrument, which may represent a significant risk factor to the patient. The flowmeter also administers and measures small volumes of fluid such as saline via fluid line 107 from an IV bag 108 suspended above the flowmeter. The flowmeter apparatus also controls the volume of fluid infusion, displays values of the various measured parameters and provides audible alarms if conditions of blood flow become dangerous.

The flowmeter apparatus basically comprises measurement channel 101, delivery unit 109, sensor unit 110, and control unit 111. Measurement channel 101 has a predetermined volume between first position 156 and second position 124 and comprises commercially available clear vinyl blood tubing of a fixed, premeasured length between six and sixteen inches and a 0.22 inch internal diameter. Similarly, lines 102, 103, and 105–107 comprise various lengths of commercially available clear vinyl blood tubing. First measurement position 156 of the measurement channel is located at the entrance of the tubing or at the junction of T-connector 114. Second measurement position 124 of the channel is located downstream of the first position and between a photoemitter and a photodetector of the sensor unit. The flowmeter apparatus utilizes the measurement positions and volume of the channel to calculate the rate of flow of blood through the channel.

The delivery unit produces an interface between the incoming arterial blood and another fluid, such as saline, at first position 156 of measurement channel 101. Arterial line 102 passes through longitudinal blood line cavity 112 and clamping cavity 122 of clamp block 113. This clamp block is fashioned from an aluminum block and maintains the positions of the tubular lines passing through the longitudinal and clamping cavities formed therein. The arterial line passes through longitudinal blood line cavity 112 and clamping cavity 122 and connects to channel 101 via T-connector 114. Similarly, fluid line 107 passes through longitudinal fluid line cavity 115 of empty tube sensor block 116 and longitudinal fluid line cavity 117 and clamping cavity 122 of clamp block 113. Fluid line also connects to channel 101 via T-connector 114.

Delivery unit 109 includes clamp unit 118 under control of control unit 111 for selectively administering a bolus of saline fluid from fluid line 107 into the blood from arterial line 102. As a result, the saline bolus produces a leading and a trailing interface in measurement channel 101. The arterial line transports blood from the patient to measurement channel 101. Fluid line 107 transports the other fluid, such as saline, to the measurement channel.

Figure 3:
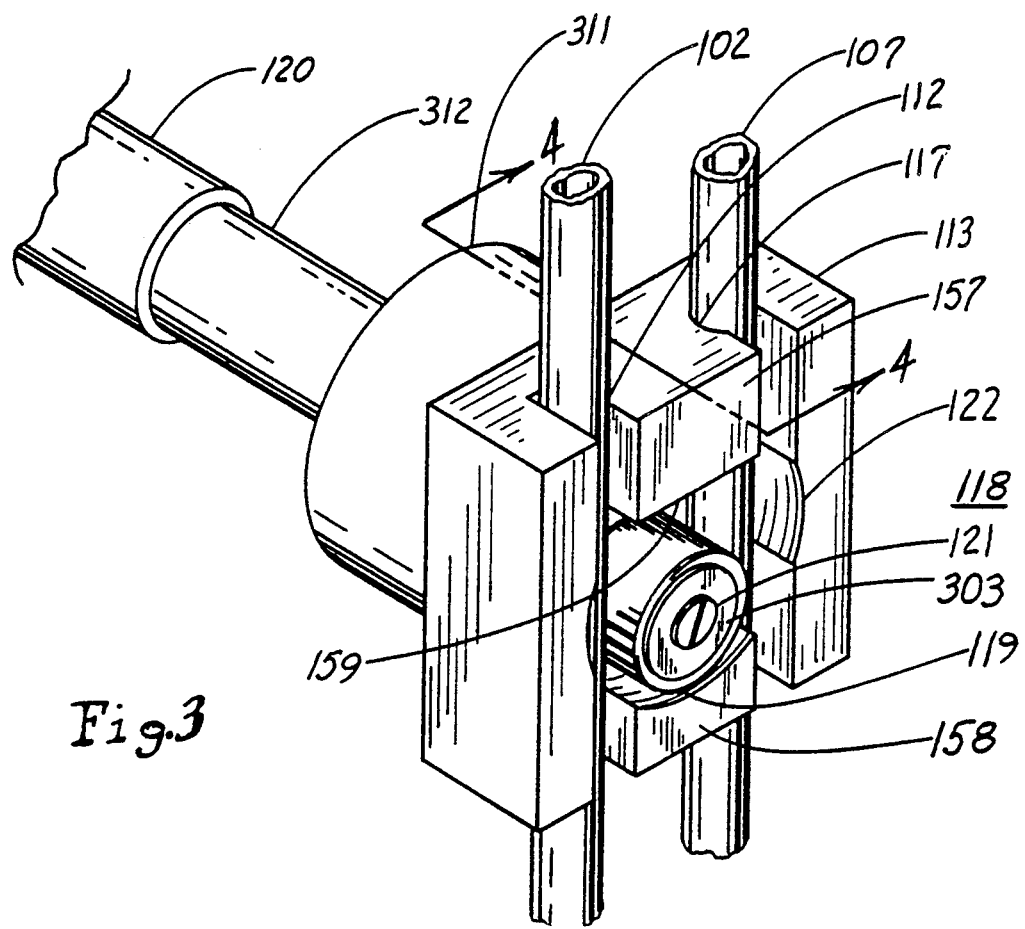
FIG. 3 depicts a perspective view of the clamp unit of the flowmeter apparatus of FIG. 1.

Depicted in FIG. 3 is a perspective view of clamp unit 118 including clamp block 113, roller 119, and DC electric motor 120. Tubular arterial blood line 102 passes through longitudinal cavity 112 that extends through clamping cavity 122. Similarly, tubular saline fluid line 107 passes through longitudinal cavity 117 that extends through clamping cavity 122. Upper and lower segments 157 and 158 of the clamp block extend over a portion of the longitudinal cavities to confine and maintain the position of the tubular lines extending through the longitudinal cavities. As shown in FIG. 1, roller 119 has been operated in a counterclockwise direction by motor 120 to a resting position on flat surface 159 of clamping cavity 122. As a result, roller 119 compresses saline fluid line 107 and occludes the flow of saline therein. Roller 119, in this counterclockwise resting position, does not effect the flow of blood in arterial line 102. As shown in FIG. 3, roller 119 has been rotated by motor 120 in a clockwise direction from counterclockwise resting position to a neutral position opposite flat clamping cavity surface 159 between lines 102 and 107. Roller 119 in this neutral position does not effect the flow of blood or saline in lines 102 and 107, respectively.

Figure 4:
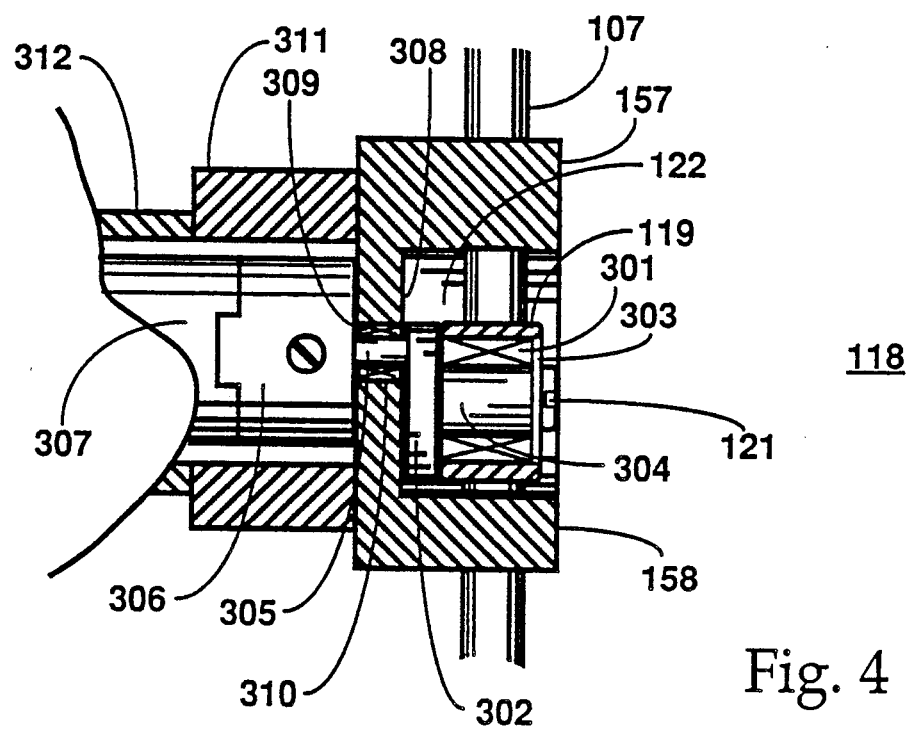
FIG. 4 depicts a cross-sectional view of the clamp unit of FIG. 3 taken along line 4—4.

Depicted in FIG. 4 is a cross-sectional view of clamp unit 118 taken along the line 4—4 in FIG. 3 with roller 119 in the neutral position. As shown, plastic material roller 119 is mounted on shaft 304 with well-known bearings 301. The roller and bearings are held in place against circular disk 302 with well-known retaining plate 303 and fastener 121. Shaft 304 is centrally affixed to disk 302. Disk 302 is eccentrically affixed to shaft 305 which is also connected to motor 120 via tongue and groove coupling collars 306 and 307. Shaft 305 extends through clamping cavity face 308 through aperture 309 with a bearing 310 positioned therein. Cylindrical mounting flanges 311 and 312 position the motor and collars 306 and 307 with respect to the clamping block.

Returning attention to FIG. 1 and FIG. 3, motor 120 is a well-known and commercially available DC electric motor that operates bidirectionally in either a clockwise or counterclockwise direction under the control of control unit 111 via well-known drive circuit and buffer 123. When the motor continues to rotate the neutral position roller in a clockwise direction, the roller will come to a clockwise resting position on flat surface 159 and compress arterial line 102. As a result, the flow of blood is occluded in the arterial line. Saline fluid flows in fluid line 107 producing a leading blood/saline interface at position 156 of channel 101. When the roller is returned to the counterclockwise resting position, the flow of saline is occluded, thereby administering a bolus of saline fluid to the measurement channel and producing a trailing saline/blood interface at first position 156 of the measurement channel. Thus, a bolus of saline is administered to the blood with leading and trailing interfaces for passage through measurement channel 101. Since saline remains in fluid line 107 between roller 119 and T-connector 114, the transmission of control signals to DC motor 120 to open and occlude fluid line 107 is utilized by controller 111 as an indication of when the leading and trailing interfaces are produced at first position 156 in measurement channel 101. Each interface is detectable due to the change in concentration of the hematocrit of the blood.

Figure 5:
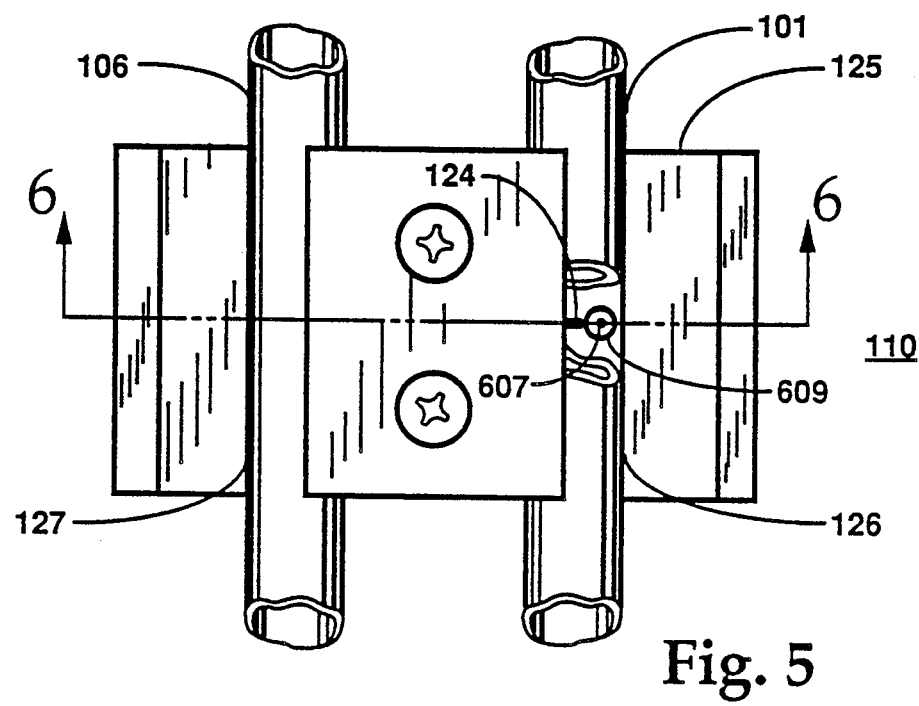
FIG. 5 depicts a top view of the sensor unit of the flowmeter apparatus of FIG. 1.
Figure 6:
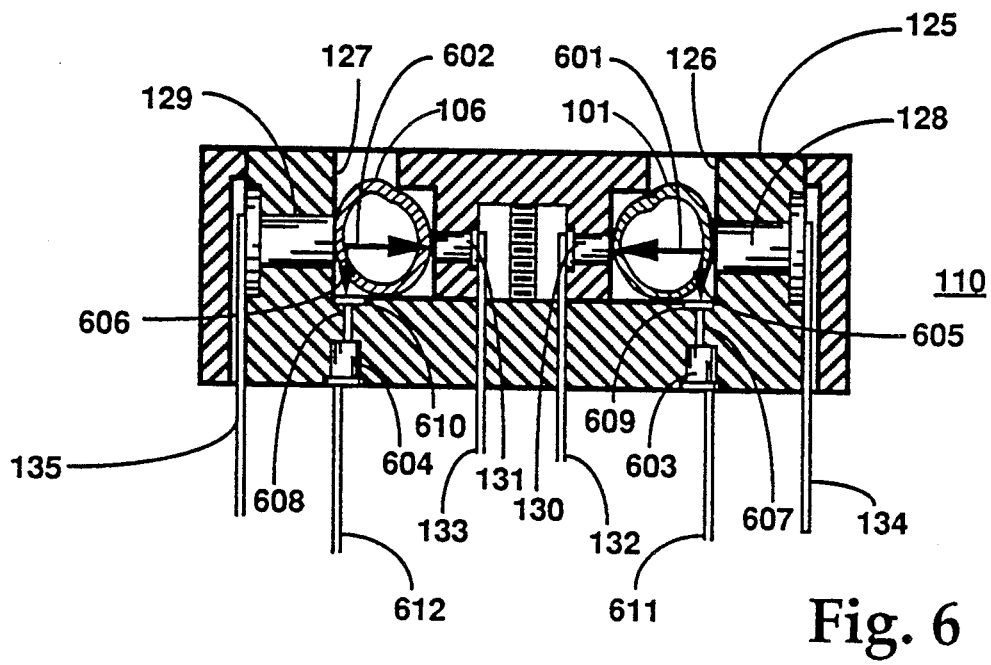
FIG. 6 depicts a cross-sectional view of the sensor unit of FIG. 5 taken along line 6—6.

Depicted in FIG. 5 is sensor unit 110 that is responsive to the leading and trailing interfaces at second position 124 in measurement channel 101 for producing an output signal that is indicative of when an interface is at the second position. Sensor unit 110 includes a nonconductive black plastic sensor block 125 having arterial and venous longitudinal cavities 126 and 127 for maintaining the position of the vinyl tube of measurement channel 101 and venous line 106, respectively. Depicted in FIG. 6 is a cross-sectional view of sensor unit 110 taken along the line 6—6 in FIG. 5. As shown, the sensor unit also includes photoemitters 128 and 129 such as commercially available 5 milliwatt lasers with a built-in photodiode and feedback circuit for directing respective optical signal 601 and 602 having a constant intensity into the vinyl tubing of measurement channel 101 and venous line 105, respectively. Second position 124 in channel 101 is determined by the location of the optical signal emitted from and directed into the vinyl tubing from photoemitter 128. Similarly, photoemitter 129 directs optical signal 602 having a constant intensity into the vinyl tubing of the venous line 106.

The sensor unit further includes transmission photodetectors 130 and 131 positioned directly across from respective photoemitters 128 and 129 for receiving optical signals 601 and 602 transmitted through the interpositioned vinyl tubing, respectively. Each of these photodetectors, such as a well-known photodiode, receives the transmitted optical signal that has been transmitted completely through the vinyl tubing and any fluid contained therein. Photodetector 130 senses the intensity of optical signal 601 transmitted through the channel at second position 124 for producing an electrical output signal that is indicative of the intensity of optical signal 601. A change in the intensity of optical signal 601 transmitted through the channel is utilized to indicate when either a leading or trailing blood/saline interface is at the second position in the channel. This change in the intensity of the optical signal is due to changes in the hematocrit of the fluid within the channel or to a change from liquid to air within the channel. Thus, the photodiode is a sensitive indicator of the passage of either leading or trailing blood/saline interface or the replacement of blood by air in the tubing. Photodiode 130 is also responsive to optical signal 601 for producing another electrical unit output signal that is indicative of small bubbles or foam in the arterial measurement channel. The electrical output signals from photodetector 130 are conducted to control 111 via conductor 132. Similar to photodetector 130, photodetector 131 is positioned across from photoemitter 129 for receiving optical signal 602 that is transmitted through venous line 106. In response to intensity changes in optical signal 602, photodetector 130 produces an electrical output signal indicative of small bubbles and foam in venous line 106. This output signal is conducted to control unit 111 via conductor 133. Control unit 111 controls the operation of photoemitters 128 and 129 via conductors 134 and 135, respectively.

Sensor unit 110 also includes a second pair of photodetectors 603 and 604 for receiving respective optical signals 605 and 606 reflected from measurement channel 101 and venous line 106, respectively. Optical signals 605 and 606 are reflected from the interfaces established between the vinyl tubing and blood flowing therein. These reflectance photodetectors are positioned in the bottom of sensor block 125 at a 90° angle to the photoemitter to receive the reflected optical signals through small diameter cylindrical passageways 607 and 608. These passageways lead from the bottom of the cavities and are positioned to receive the optical signals reflected from the precise location at which the optical signal from the photoemitter meets the blood within the tubing. Transparent disks 609 and 610 are placed at the opening of passageways 607 and 608, respectively. In response to these reflected optical signals, photodetectors 603 and 604 produce electrical output signals in which changes in the DC and AC voltages are indicative of pulsating blood flow, particulate content of the blood, and the foam and bubble content of the blood. Photodetectors 603 and 604 conduct these electrical output signals to control unit via respective conductors 611 and 612.

A more detailed description of the operation and use of these reflectance photodetectors are provided in the afore-referenced patent of one of the present inventors and in two other publications: "The Biological-HD: Hemodialysis Simplified," Ash SR, Blake DE, Carr DJ, Baker K, and Echard TG, in *Artificial Organs: Proceedings of the International Symposium on Artificial Organs, Biomedical Engineering, and Transplantation in Honor of the 75th Birthday of Willem J. Kolff*; Andrade JD ed, VCH Publishers, NY, 1987, p. 263–277, and "Clinical Trials of the Biologic-HD; Automated Single Access, Sorbent-based Dialysis," Ash SR, Baker K, Blake DE, Carr DJ, Echard TG, Sweeney KD, Handt AE, and Wimberly AL; *Trans ASAIO*, V. 33, 1987, p. 524–531.

Referring attention again to FIG. 1, control unit 111 includes processor 136, timer 137, permanent memory 138, temporary memory 139, and address decoder and latch circuit 140 that are all interconnected by bus 141. All of these circuits are well known to those skilled in the art and may comprise, for example, Intel's 80C31 microprocessor for processor 136, erasable programmable read only memory (EPROM) 27256/27512 for permanent memory 138, 16K bytes of random access memory (RAM) comprising two Intel DS-1225 memory chips for temporary memory 139, a commercially available timer circuit for timer 137, and a commercially available address decoder and latch circuit for decoder and latch 140. Program instructions for controlling the operation of the processor are stored in permanent memory 138 along with two algorithms that will be hereinafter described. Permanent memory 138 also includes program instructions for interpreting the DC and AC voltages of photodetector 130, 131, 603, and 604 for determining a quantity representative of the blood particulate, the pulsating flow of blood, and bubbles in the blood. A specific set of program instructions for these functions is also commercially available from Ash Medical. Temporary memory 139 stores temporary data such as various time periods that are measured by timer circuit 137. Address decoder and latch 140 is utilized under the control of processor 136 for sending and receiving various control and indicator signals from delivery unit 109 and sensor unit 110. Decoder circuit 140 also interfaces with empty tube sensor 116 and weight measuring instrument 142. Control unit 111 digitally controls the operation of delivery unit 109 and, in particular, DC motor 120 via well-known drive circuit and buffer 123. Control unit 111 and drive circuit and buffer 123 communicate via communication channel 147.

Flowmeter apparatus 100 also includes a well-known analog-to-digital interface unit 143 for interfacing with sensor unit 110, weight measuring instrument 142, and empty tube sensor 116 in a well-known manner. This interface utilizes well-known amplifiers and analog-to-digital convertors for performing this analog-to-digital interface function. Analog-to-digital interface unit 143 and control unit communicate via communication channel 148. Interface unit 143 communicates with empty tube sensor 116 and strain gauge 142 via conductors 149 and 150, respectively.

Key pad 144 interfaces with control unit 111 via channel 151 and provides for operator input of commands and information to direct the operation of the apparatus. The key pad is also utilized to define acceptable limits for any measured parameter and to input an indication of the predetermined volume of measurement channel 101 between first and second positions 156 and 124.

Display unit 145 also communicates with control unit 111 via communication channel 152. For example, this display unit is a commercially available 16-character by four-line liquid crystal display which indicates information received from each sensor, present operations of the flowmeter, and input received from the key pad.

Control unit 111 also interfaces with an input/output port 146 via communication channel 153. This input/output port, such as a well-known RS232 port, provides a route for communication between the flowmeter apparatus and any other digital device such as the extracorporeal blood therapy instrument. Likewise, information may be sent to a monitoring computer or to a central alarm panel.

Timer 137 of control unit 111 is utilized for determining a time period initiated by an indication of when an interface is produced by delivery unit 109 and terminated by the output signal from sensor unit 110, which indicates when the saline bolus interfaces are at second position 124 in the channel. Program-controlled processor 136 utilizes a predetermined algorithm stored in permanent memory 138 to calculate the blood flow rate in response to the measured time period. A second algorithm is also utilized by the processor for calculating an average flow rate. A plurality of time periods, each being initiated by a successive production of a saline bolus in the blood passing through measurement channel 101, are determined by the timer circuit. Each of these time periods are then stored in temporary memory 139 and used by the second algorithm for calculating the average blood flow rate. When calculated, the control unit sends the rate to display unit 145 to provide a visual indication of the calculated rate.

Empty tube sensor 116 included in the flowmeter basically comprises a pair of optical devices such as a light emitting diode 154 and a photodetector 155 positioned on opposite sides of fluid line 107 passing through longitudinal cavity 115 of the sensor block. Should IV bag 108 run out of fluid during fluid administration to the arterial line, the empty tube sensor will emit a large AC signal as the air-fluid interface passes between the optical device pair. Subsequently, the pair will emit a lower DC voltage when air replaces the fluid in the tube due to reflection at the vinyl/air interface.

Strain gauge 142 is a well-known weight measuring device comprised of a solid state structure designed to deform with increasing weight on it. By way of example, four surfacemounted resistors whose electrical resistance changes in proportion to deformation are utilized to indicate a change in the weight of the fluid bag. The change in electrical resistance is utilized by the apparatus to accurately measure changes in the weight of the IV bag, thereby accurately reflecting the volume of fluid removed therefrom.

A method of determining a rate of flow of blood in channel 101 basically comprises producing an interface between the blood and another fluid, such as saline, at first position 156 in the measurement channel and a first indication of the production of the interface; producing a second indication of when the interface is at second position 124 in the channel, and calculating the rate of flow of blood in the channel utilizing a predetermined algorithm, an indication of the channel volume, and the first and second indications. The measurement channel has a predetermined volume, which is manually measured and determined. An indication of this predetermined volume may be provided to the processor via input keyboard 144 or built into the software if the volume is to be kept constant.

The basic concept of measuring blood flow rate is as follows. Normally during operation, clamp unit 118 occludes fluid line 107 in clamping cavity 122. While arterial blood is flowing through input line 102, roller 119 is quickly rotated to occlude the arterial line, and then returned to its usual position occluding the saline fluid line. Total cycle time is less than 0.5 seconds. During rotation of the roller, approximately a 4 cc bolus of saline fluid is delivered into the arterial line due to the negative pressure in this line. Measurement channel photodetector 130 records an increase in voltage as the front of the bolus passes through the sensor unit. This transmission photodetector then records a decrease in voltage as the trailing edge of the bolus passes through the sensor unit. The time between the closing of the clamp on the saline fluid line and the passage of the trailing edge of the bolus through the sensor unit reflects the flow rate of the blood through the flow measurement channel under normal operating conditions. This flow rate is realistic and accurate, since the roller pump is pulling against the hydraulic resistance of the inlet needle or catheter when the clamp returns to its normal position. The accuracy of this measurement is only diminished by the degree to which the saline fluid bolus perturbs the normal volumes and pressures within the system. This perturbation is minimized if the roller clamp moves quickly and the saline fluid bolus is small. Since roller pumps have varying flow during each half cycle, determining the roller pump revolution rate and performing bolus measurements at specific times during various revolutions allows calculation of an accurate average flow rate.

In a single-needle blood therapy system, flow rate varies greatly throughout each inflow cycle. Performing bolus measurements at specific times throughout various inflow cycles allows calculation of an accurate average flow rate. When a saline bolus is injected into the blood flow measurement channel, the time it takes the trailing interface of the saline bolus to pass through the channel is measured as the difference between the measured time of closure of the saline fluid line and the time of rapid decrease of the transmission photodetector voltage of the sensor unit. The mathematics for calculating instantaneous flow rates is straightforward. There are two terms of a simple equation:

Instantaneous flow rate (IFR)=(Volume in tubing segment)/transit time.

Since transit time is measured in seconds and flow rate is usually measured in milliliters per minute, the exact flow rate algorithm is:

Blood flow rate (BFR)=(V×60 sec/min)/T;

where BFR is the instantaneous blood flow rate, V is the volume of the flow measurement channel in milliliters, and T is the measured transit time in seconds.

To measure average blood flow rate in this system with a cyclically varying blood inflow rate, a second algorithm is utilized:

BTR=(BFR/N)/(Total/Inflow);

where BTR is the average inflow blood treatment rate, N is the number of data points, Inflow is the cycle time over which several measurements are made, Total is the total cycle time in seconds, and Total/Inflow is greater than one per single access devices in which the blood flow is interrupted to allow outflow through the same access lumen.

Figure 2:
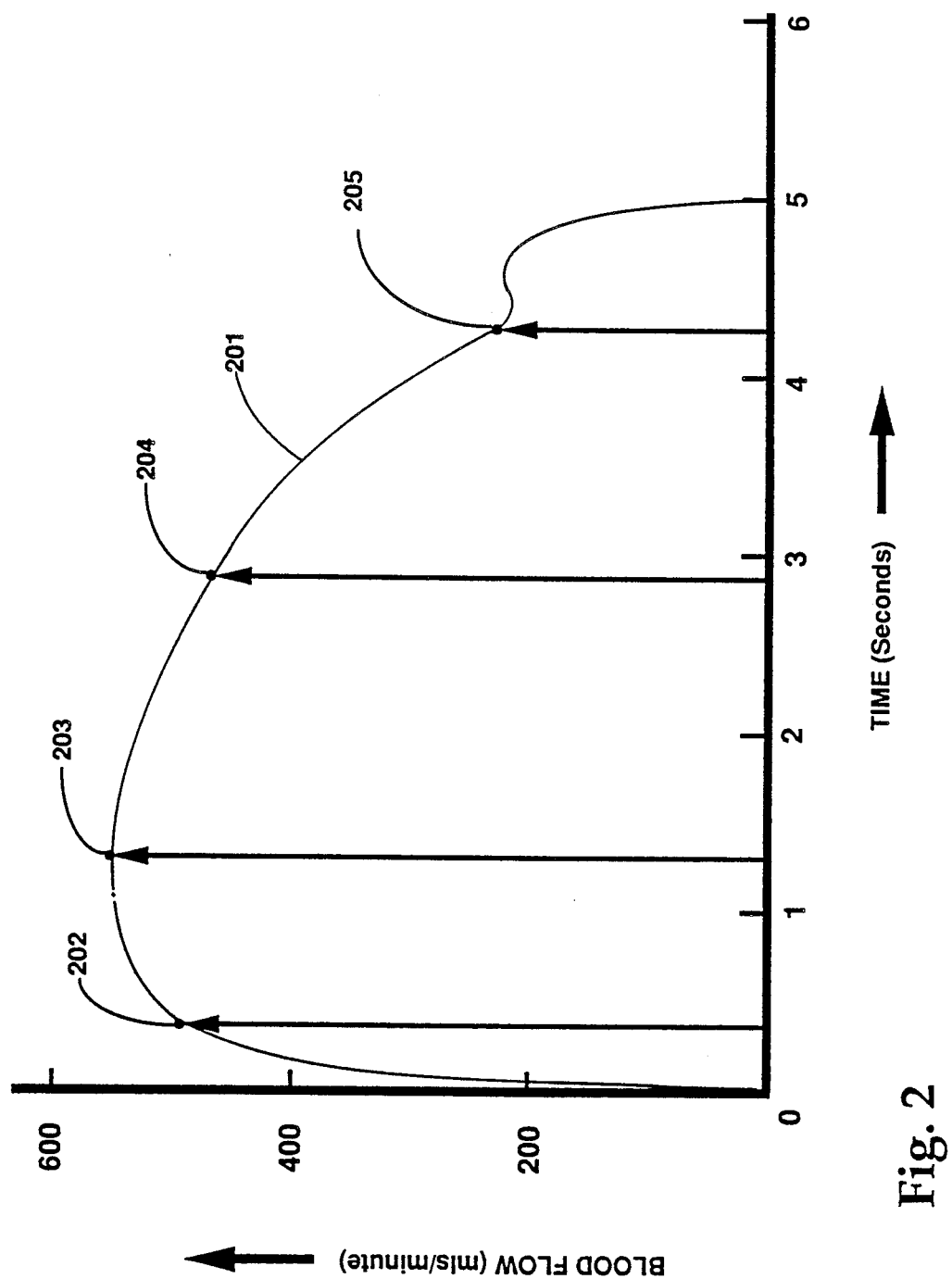
FIG. 2 depicts actual and measured flow rate curves for blood flowing through the apparatus of FIG. 1 during one inflow cycle of a single access instrument.

Depicted in FIG. 2 is the actual flow curve 201 for blood flowing into a single-access extracorporeal blood therapy instrument, such as the Biologic HD-Dialysis instrument described in the afore-referenced patent. This figure also includes the instantaneous blood flow rate measurements 202-205, measured at four different times of the cycle, during four successive inflow cycles. The duration of the measurement is dependent on the flow rate at the time of measurement. Averaging these four measured rates and accounting for the time of inflow and outflow portions of the cycle gives a close approximation of the average blood treatment rate (BTR). Even with the widely varying flow rate of a single access therapy instrument, the flowmeter apparatus utilizing these calculations has provided measurements of blood flow treatment rates within 5% of the actual rate. For dual access blood treatment instruments with an arterial side roller pump, the flow rate varies less. Analyzing instantaneous blood flow during successive cycles of the roller pump results in an even more accurate measurement of the blood treatment rate.

Fluid addition to blood tubing of a blood therapy instrument is usually performed manually by opening and closing clamps and visually measuring the amount of fluid delivered. This flowmeter apparatus allows this fluid addition to be performed automatically, with accurate measurement of total fluid volume delivered to the tubing and to the patient. This avoids the entry of air into the tubing should the fluid container empty. The operator can define a desired amount of fluid to be delivered as a "bolus" at the start of a treatment. To accomplish this, clamp unit 118 closes the arterial line while opening fluid line 107. Strain gauge 142 measures the amount of delivered fluid. When the desired amount is infused, the clamp unit under the control of control unit 111 closes the fluid line while opening arterial line 102. The empty tube sensor will cause the closure of the clamp unit on the fluid line whenever it senses that the fluid bag is empty. The response time is fast enough to avoid air entry to the arterial line and the membrane unit of blood therapy instrument 104.

In a more sophisticated operation, the flowmeter apparatus also automatically delivers defined amounts of fluid into the arterial line on preset intervals. For example, if the patient has reached "dry weight," the apparatus infuses fluid at the same rate at which it was removed by the blood therapy instrument. Alternatively, if the patient's weight is to be increased during the procedure, the apparatus can be directed to deliver a certain volume of fluid over the expected time of the procedure. Finally, to diminish the need for anticoagulant, the apparatus delivers a bolus of approximately 100 cc each ½ hour, rinsing accumulated blood proteins and clotting factors from the surfaces of the membrane unit of the blood therapy instrument.

An additional function of the flowmeter apparatus is to measure the internal volume of the blood circuit of the blood therapy instrument. After a 100 cc or greater bolus of fluid is administered, the venous line sensor and timer determines the time between the appearances of the leading and trailing interfaces. The control unit calculates the transit time for the trailing interface of the fluid bolus. Using this information and the known average blood flow rate, the control unit calculates the volume of blood in the blood therapy instrument, principally the volume within the membrane unit. Changes in this membrane unit volume within a treatment or over several treatments is indicative of clotting within one or more of the blood pathways within the membrane unit.

The flowmeter apparatus is also utilized to rinse blood from the blood therapy instrument. At a designated time, clamp unit 118 closes the arterial line and opens the other fluid line. Priming fluid is then continually drawn into the other arterial tubing and passes through the membrane unit of the blood therapy instrument. Rinsing is complete when the fluid within the venous line becomes low in hematocrit. This is detected by the use of optical device pair 129 and 131. When dialyzers are rinsed manually, the operator observes the venous line and stops rinsing when the line appears "light pink." The photometer of the sensor unit yields a low voltage signal when the hematocrit falls below 3%. Based on this output signal, the apparatus continually rinses the dialyzer it until is nearly completely devoid of blood cells, then automatically stops the rinsing. If the roller pump is then stopped, the clamp unit moves to a neutral position opening both arterial and fluid lines. Hydrostatic pressure within the prime fluid line will then allow fluid to rinse the arterial line. The volume of the prime fluid rinsing the arterial line is either visually monitored or preset through the key pad. When rinsed sufficiently, clamp unit 118 is directed to occlude fluid line 107.

During the rinsing procedure, the venous channel of the apparatus monitors venous line 106 for bubbles and sounds an alarm if bubbles should progress toward the patient. The arterial channel can assure that fluid is passing toward the membrane unit of the blood therapy instrument rather than blood, thus insuring the proper functioning of delivery unit 109.

It is to be understood that the above-described method and apparatus for determining the flow rate of blood through a measurement channel for use with an extracorporeal blood therapy instrument is merely an illustrative embodiment of the principles of this invention and that numerous other devices and methods may be devised by those skilled in the art without departing from the spirit and scope of this invention.

What is claimed is:

1. For use with an extracorporeal blood therapy instrument, apparatus for determining a rate of flow of blood through a channel, comprising:
   delivery means for producing a trailing interface of another fluid and between said blood and said another fluid at a first predetermined position in said channel;
   sensor means for producing an output signal indicative of when said trailing interface is at a second predetermined position in said channel, said channel having a predetermined volume between said first and second predetermined positions; and
   control means utilizing a predetermined algorithm and an indication of said volume and responsive to said output signal and an indication of when said trailing interface is produced for calculating said blood flow rate through said channel.

2. The apparatus of claim 1 wherein said delivery means includes clamp means under control of said control means for selectively administering a bolus of said other fluid into said blood for producing said trailing interface.

3. The apparatus of claim 1 wherein said delivery means includes first means for transporting said blood, second means for transporting said other fluid, and connector means for inserting a bolus of said other fluid into said blood for producing said trailing interface.

4. The apparatus of claim 3 wherein said delivery means further includes clamp means under control of said control means for selectively occluding said flow of said blood and a flow of said other fluid in said first and second means, respectively.

5. The apparatus of claim 4 wherein said clamp means includes a clamping cavity and electric metor means under control of said control means for operating roller means in said clamping cavity and further including said roller means eccentrically connected to said motor means for selectively compressing said first and second means.

6. The apparatus of claim 1 wherein said sensor means includes photodetector means responsive to an optical signal from said channel for producing said output signal.

7. The apparatus of claim 6 wherein said sensor means further includes photoemitter means for directing said optical signal having a predetermined intensity into said channel, a predetermined change of the intensity of said optical signal from said channel being indicative of when said trailing interface is at said second position in said channel.

8. The apparatus of claim 1 wherein said sensor means includes photodetector means responsive to an optical signal from said channel for producing a second output signal indicative of a bubble in said blood.

9. The apparatus of claim 8 wherein said control means includes means responsive to said second output signal for determining a quantity for said bubble.

10. The apparatus of claim 1 wherein said sensor means includes photodetector means responsive to an optical signal from said channel for producing a second output signal indicative of particles in said blood.

11. The apparatus of claim 9 wherein said control means includes means responsive to said second control signal for determining a quantity for said particles.

12. The apparatus of claim 1 wherein said control means includes timer means for determining a time period initiated by said indication of when said trailing interface is produced and terminated by said output signal and further including processor means utilizing said predetermined algorithm and said indication of said volume and responsive to said time period for calculating said blood flow rate.

13. The apparatus of claim 12 wherein said control means includes means responsive to said second output signal for determining a quantity for said pulsating blood flow.

14. The apparatus of claim 1 wherein said sensor means includes photodetector means responsive to an optical signal from said channel for producing a second output signal indicative of pulsating flow of said blood.

15. The apparatus of claim 14 further comprising display means for displaying a frequency for said pulsating blood flow.

16. The apparatus of claim 14 wherein said control means includes memory means for storing a plurality of said time periods and wherein said processor means utilizes a second predetermined algorithm and said indication of said volume and is responsive to said time periods for calculating an average blood flow rate.

17. The apparatus of claim 1 further comprising means for determining the amount of said other fluid delivered to said channel.

18. The apparatus of claim 14 further comprising sensor means for detecting a delivery of said other fluid to said channel.

19. For use with an extracorporeal blood therapy instrument, apparatus for determining a rate of flow of blood in a channel, comprising:
   said channel having a predetermined volume between first and second predetermined positions therein;
   a first flexibly resilient tube for transporting said blood;
   a second flexibly resilient tube for transporting another fluid;
   a connector connected to said first and second tubes and said channel for inserting a bolus of said other fluid into said blood for producing an interface at said first predetermined position in said channel;
   a clamp unit including an electric motor under control of a processor and a roller eccentrically connected to said motor for selectively occluding said flow of said blood and a flow of said other fluid in said first and second tubes for producing said bolus of said other fluid;
   a laser for directing an optical signal having a predetermined intensity into said channel at said second predetermined position;
   a first photodetector responsive to said optical signal transmitted through said channel at said second predetermined position for producing a first output signal indicative of when said interface is thereat and a second output signal indicative of bubbles in said blood;
   a second photodetector responsive to said optical signal reflected from said channel for producing a third output signal indicative of particles in said blood and a fourth output signal indicative of a pulsating flow of said blood;
   a timer circuit for determining a time period initiated by an indication of when said interface is produced and terminated by said first output signal;
   a processor utilizing a predetermined algorithm and an indication of said volume and responsive to said time period for calculating said blood flow rate;
   said processor being further responsive to said second through fourth output signals for determining a quantity for said bubbles, said particles, and said pulsating blood flow, respectively; and
   a display unit for visually displaying said blood flow rate and said quantity of said bubbles, said particles, and said pulsating blood flow.

20. For use with an extracorporeal blood therapy instrument, method for determining a rate of flow of blood in a channel, comprising:
   producing a trailing interface of another fluid and between said blood and said another fluid at a first predetermined position in said channel and a first indication of a production of said trailing interface;
   producing a second indication of when said trailing interface is at a second predetermine position in said channel, said channel having a predetermined volume between said first and second positions; and
   calculating said rate of said flow of said blood in said channel utilizing a predetermine algorithm, said first and second indications, and an indication of said predetermined volume.

21. The method of claim 20 wherein calculating said blood flow rate includes determining a time period between said first and second indications and calculating said blood flow rate utilizing said determined time period.

22. The method of claim 21 further comprising producing a plurality of said trailing interfaces and indications thereof, producing indications of when each of said trailing interfaces is at said second position in said channel, determining a plurality of time periods each between the production of said each trailing interface and a determination of when said each trailing interface is at said second position, and calculating an average rate of said flow of said blood in said channel utilizing a second algorithm utilizing said channel volume and said plurality of time periods.

23. The method of claim 20 wherein producing said trailing interface includes selectively administering a bolus of said other fluid to said blood.

24. The method of claim 20 wherein producing said trailing interface includes transporting said blood in a first resilient flexible tube and said other fluid in a second resilient flexible tube; interconnecting said first and second tubes with said channel; and selectively occluding said blood flow and a flow of said other fluid in said first and second tubes, respectively.

25. The method of claim 20 wherein producing said second indication includes directing an optical signal having a predetermined intensity into said channel at said second position and sensing a predetermined change in the intensity of said optical signal from said channel.

26. The method of claim 20 further comprising visibly displaying said blood flow rate when calculated.

27. For use with an extracorporeal blood therapy instrument, apparatus for determining a rate of flow of blood through a channel, comprising:
   first means for transporting said blood, second means for transporting another fluid, and connector means for inserting a bolus of said other fluid into said blood for producing an interface between said blood and said other fluid at a first predetermined position in said channel;
   sensor means for producing an output signal indicative of when said interface is at a second predetermined position in said channel, said channel having a predetermine volume between said first and second predetermined positions;
   control means utilizing a predetermined algorithm and an indication of said volume and responsive to said output signal and an indication of when said interface is produced for calculating said blood flow rate through said channel; and
   clamp means under control of said control means for selectively occluding said flow of said blood and a flow of said other fluid in said first and second means, respectively.

28. The apparatus of claim 27 wherein said clamp means includes a clamping cavity and electric motor means under control of said control means for operating roller means in said clamping cavity and further including said roller means eccentrically connected to said motor means for selectively compressing said first and second means.

29. For use with an extracorporeal blood therapy instrument, apparatus for determining a rate of flow of blood through a channel, comprising:

delivery means for producing an interface between said blood and another fluid at a first predetermined position in said channel;

sensor means for producing an output signal indicative of when said interface is at a second predetermined position in said channel, said channel having a predetermined volume between said first and second predetermined positions;

control means utilizing a predetermine algorithm and an indication of said volume and responsive to said output signal and an indication of when said interface is produced for calculating said blood flow rate through said channel; and means for determining the amount of said other fluid delivered to said channel.

30. For use with an extracorporeal blood therapy instrument, method for determining a rate of flow of blood in a channel, comprising:

producing an interface between said blood and another fluid at a first predetermined position in said channel and a first indication of a production of said interface, said producing including transporting said blood in a first resilient flexible tube and said other fluid in a second resiliently flexible tube interconnecting said first and second tubes with said channel, and selectively occluding said blood flow and a flow of said other fluid in said first and second tubes, respectively;

producing a second indication of when said interface is at a second predetermine position in said channel, said channel having a predetermined volume between said first and second positions; and calculating said rate of said flow of said blood in said channel utilizing a predetermined algorithm, said first and second indications, and an indication of said predetermined volume.

* * * * *